United States Patent
Tehrani et al.

(10) Patent No.: US 10,206,796 B2
(45) Date of Patent: Feb. 19, 2019

(54) MULTI-STRAND IMPLANT WITH ENHANCED RADIOPACITY

(71) Applicant: DEPUY SYNTHES PRODUCTS, INC., Raynham, MA (US)

(72) Inventors: Ramin Tehrani, Hialeah, FL (US); Robert Slazas, Miami, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 349 days.

(21) Appl. No.: 14/469,862

(22) Filed: Aug. 27, 2014

(65) Prior Publication Data

US 2016/0058524 A1    Mar. 3, 2016

(51) Int. Cl.

| | |
|---|---|
| *A61F 2/86* | (2013.01) |
| *A61F 2/06* | (2013.01) |
| *A61F 2/07* | (2013.01) |
| *A61B 19/00* | (2006.01) |
| *D03D 3/02* | (2006.01) |
| *D04C 1/02* | (2006.01) |
| *D04C 1/06* | (2006.01) |

(52) U.S. Cl.
CPC ............... *A61F 2/86* (2013.01); *A61B 19/54* (2013.01); *A61F 2/06* (2013.01); *A61F 2/07* (2013.01); *D03D 3/02* (2013.01); *D04C 1/02* (2013.01); *D04C 1/06* (2013.01); *A61F 2250/0032* (2013.01); *A61F 2250/0098* (2013.01); *D10B 2509/06* (2013.01)

(58) Field of Classification Search
CPC ................ A61F 2250/0017; A61F 2250/0032
See application file for complete search history.

(56) References Cited

U.S. PATENT DOCUMENTS

| | | | |
|---|---|---|---|
| 5,423,849 | A | 6/1995 | Engelson |
| 5,645,558 | A | 7/1997 | Horton |
| 5,662,622 | A | 9/1997 | Gore |
| 5,916,235 | A | 6/1999 | Guglielmi |
| 6,626,936 | B2 | 9/2003 | Stinson |
| 6,673,106 | B2 | 1/2004 | Mitelberg |
| 6,818,013 | B2 | 11/2004 | Mitelberg |
| 6,833,003 | B2 | 12/2004 | Jones |
| 6,899,914 | B2 | 5/2005 | Schmitz |

(Continued)

FOREIGN PATENT DOCUMENTS

| | | |
|---|---|---|
| CN | 101234046 A | 8/2008 |
| CN | 103347466 A | 10/2013 |

(Continued)

OTHER PUBLICATIONS mig-welding.co.uk; Excerpt from with comment of Jun. 29, 2011 on pictures of welds.

(Continued)

*Primary Examiner* — Thomas J Sweet
*Assistant Examiner* — Megan Wolf

(57) ABSTRACT

An implant for medical use, and methods of making same, having a body formed of a plurality of single strands of a first material. The body further includes at least one multi-strand of radiopaque material incorporated among the single strands, the multi-strand having at least two side-by-side filaments of radiopaque material that lie substantially contiguous to each other over substantially the entire length of the multi-strand.

5 Claims, 3 Drawing Sheets

(56) References Cited

U.S. PATENT DOCUMENTS

| | | |
|---|---|---|
| 6,918,928 B2 | 7/2005 | Wolinsky |
| 6,955,685 B2 | 10/2005 | Escamilla |
| 6,960,227 B2 | 11/2005 | Jones |
| 6,970,734 B2 | 11/2005 | Eidenschink |
| 7,001,422 B2 | 2/2006 | Escamilla |
| 7,037,331 B2 | 5/2006 | Mitelberg |
| 7,208,008 B2 | 4/2007 | Clarke |
| 7,267,685 B2 | 9/2007 | Butaric |
| 7,291,167 B2 | 11/2007 | DiCaprio |
| 7,344,559 B2 | 3/2008 | Gray |
| 7,462,190 B2 | 12/2008 | Lombardi |
| 7,480,973 B2 | 1/2009 | Miller |
| 7,641,647 B2 | 1/2010 | Gunderson |
| 7,761,138 B2 | 7/2010 | Wang |
| RE42,244 E | 3/2011 | Boatman |
| 7,913,371 B2 | 3/2011 | Klocke |
| 7,985,213 B2 | 7/2011 | Parker |
| 8,021,418 B2 | 9/2011 | Gerberding |
| 8,142,456 B2 | 3/2012 | Rosqueta |
| 8,152,833 B2 | 4/2012 | Zaver |
| 8,187,316 B2 | 5/2012 | Kuppurathanam |
| 8,394,119 B2 | 3/2013 | Zaver |
| 8,579,959 B2 | 11/2013 | Ducke |
| 2001/0021873 A1 | 9/2001 | Stinson |
| 2002/0095205 A1 | 7/2002 | Edwin |
| 2003/0055493 A1 | 3/2003 | Carpenter |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0044399 A1 | 3/2004 | Ventura |
| 2004/0073291 A1 | 4/2004 | Brown |
| 2004/0167619 A1 | 8/2004 | Case |
| 2004/0254637 A1 | 12/2004 | Yang |
| 2005/0049670 A1 | 3/2005 | Jones |
| 2005/0148866 A1 | 7/2005 | Gunderson |
| 2005/0234536 A1 | 10/2005 | Mitelberg |
| 2005/0257674 A1* | 11/2005 | Nishri ............... D04C 1/02 87/11 |
| 2005/0283220 A1 | 12/2005 | Gobran |
| 2005/0288775 A1 | 12/2005 | Dong |
| 2006/0015173 A1 | 1/2006 | Clifford |
| 2007/0060994 A1 | 3/2007 | Gobran |
| 2007/0156230 A1 | 7/2007 | Dugan |
| 2007/0208373 A1 | 9/2007 | Zaver |
| 2007/0238979 A1 | 10/2007 | Huynh |
| 2008/0009938 A1 | 1/2008 | Huang |
| 2008/0243227 A1 | 10/2008 | Lorenzo |
| 2008/0288046 A1 | 11/2008 | Hemerick |
| 2009/0076594 A1 | 3/2009 | Sabaria |
| 2010/0069948 A1 | 3/2010 | Veznedaroglu |
| 2010/0234935 A1 | 9/2010 | Bashiri |
| 2012/0168022 A1 | 7/2012 | Rasmussen |
| 2013/0060323 A1 | 3/2013 | McHugo |
| 2013/0274849 A1 | 10/2013 | Zaver |

FOREIGN PATENT DOCUMENTS

| | | |
|---|---|---|
| DE | 202008014828 U1 | 2/2009 |
| DE | 102011015995 A1 | 10/2012 |
| EP | 0894505 A2 | 2/1999 |
| EP | 1488763 A2 | 12/2004 |
| EP | 1634546 A1 | 3/2006 |
| EP | 2545887 A1 | 1/2013 |
| WO | WO 2001058384 A1 | 8/2001 |
| WO | WO 2001072240 A1 | 10/2001 |

OTHER PUBLICATIONS mitcale.com; Welded connections excerpt, downloaded Dec. 6, 2012.
Plug Weld Joining Two Plates; Excerpt from esabna.com, downloaded Dec. 6, 2012.
Navigate Tough Anatomy; brochure Copyright 2009; Codman & Shurtleff, Inc., 325 Paramount Drive, Raynham, Massachusetts.

* cited by examiner

MULTI-STRAND IMPLANT WITH ENHANCED RADIOPACITY

BACKGROUND OF THE INVENTION

1. Field of the Invention

The invention relates to implants within body vessels and more particularly to flow diverters, stents and other implants formed of strands of material and having radiopaque properties.

2. Description of the Related Art

Vascular disorders and defects such as aneurysms and other arterio-venous malformations are especially difficult to treat when located near critical tissues or where ready access to a malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

A number of vaso-occlusive devices have been formed of helical windings or coils of metallic wires, braided fibers, and/or woven fibers. Implants formed of non-metallic fibers, or of other materials having a low radiodensity, are difficult to track during insertion through vasculature, placement at a selected site, and possible subsequent recovery. Radiopaque fibers have been added to implants such as described by Engelson et al. in U.S. Pat. No. 5,423,849. However, the diameter of the radiopaque fibers often is very small, typically between 0.0005 to 0.005 inches, and single strands of these fibers are difficult to see during imaging by fluoroscopy or other viewing techniques. Radiopaque materials include platinum, chromium, cobalt, tantalum, tungsten, gold, silver, and alloys thereof.

Depending on the level of radiopacity desired, several techniques are known to increase visibility of an implant during imaging. Additional strands of radiopaque materials are added to the implant, the diameter of the individual strands is increased, and/or the volume of the radiopaque material is increased, such as by forming a coil. However, adding additional strands of radiopaque material may change the mechanical performance of the implant, especially for implants utilizing strands made of shape memory alloy such as Nickel Titanium. Increasing the diameter of the individual radiopaque strands for the implant not only potentially impacts the mechanical performance of the implant but also increases the wall thickness of the implant. Likewise, increasing the volume of radiopaque material by winding the radiopaque filament into a coil and adding it to the implant will impact both the mechanical performance of the implant as well as the thickness of the implant wall.

A composite yarn to reinforce a textile prosthesis is disclosed by Dong in US Patent Publication 2005/0288775. Blood flow diverters which may include braided sections are described by Gobran et al. in US Patent Publication No. 2007/0060994. Stents having radiopaque mesh to serve as filters are presented in U.S. Pat. No. 8,394,119 by Zaver et al. A woven fabric having composite yarns for endoluminal devices is described by Rasmussen et al. in US 2012/0168022.

Another type of vaso-occlusive device is illustrated in U.S. Pat. No. 5,645,558 by Horton as having one or more strands of flexible material which are wound to form a generally spherical or ovoid vaso-occlusive structure when relaxed after being placed in a vascular cavity such as an aneurysm or fistula. Similarly, U.S. Pat. No. 5,916,235 by Guglielmi cites earlier patents describing detachable coils and then discloses an expandable cage as a vaso-occlusive structure that can receive and retain one or more embolic coils after the cage is expanded within an aneurysm. A self-expandable aneurysm filling device is disclosed in US Patent Publication No. 2010/0069948 by Veznedaroglu et al.

Typically, a stent-like vascular reconstruction device is first guided beneath the aneurysm to be treated using a delivery catheter. One commercially available reconstruction product is the CODMAN ENTERPRISE® Vascular Reconstruction Device and System as described, for example, in a Navigate Tough Anatomy brochure Copyright 2009 by Codman & Shurtleff, Inc., 325 Paramount Drive, Raynham, Mass. The CODMAN ENTERPRISE® stent device is carried by a central delivery wire and initially held in place on the delivery wire in a collapsed state by a sheath-type introducer. Typically, a delivery catheter such as a PROWLER® SELECT® Plus microcatheter, also commercially available from Codman & Shurtleff and as disclosed by Gore et al. in U.S. Pat. No. 5,662,622, for example, is first positioned intravascularly with its distal tip slightly beyond the neck of the aneurysm. The tapered distal tip of the introducer is mated with the proximal hub of the delivery catheter, and the delivery wire is then advanced through the delivery catheter.

The CODMAN ENTERPRISE® stent device has a highly flexible, self-expanding closed cell design with a number of coils of radiopaque wire to serve as markers at each flared end of the device, similar to the stent illustrated in the published patent application by Jones et al., cited above. Manufacture of such markers is relatively time-consuming and expensive due to the small size of the stent and the need to wrap the radiopaque wire multiple times around struts on the stent, which is especially difficult within closed cells of the stent.

It is therefore desirable to increase radiopacity of an implant in a cost-effective manner while minimizing impacts to implant performance.

SUMMARY OF THE INVENTION

An object of the present invention is increase radiopacity of an implant having a plurality of strands while minimizing changes to implant manufacturing processes.

Another object of the present invention is to enhance radiopacity without adversely affecting performance of the implant.

A still further object of the invention is to increase radiopacity while minimizing impacts to the mechanical properties of the implant and maintaining similar wall thickness.

This invention results from the realization that two or more strands of radiopaque material can be placed side-by-side on a single carrier as a multi-strand, which can be handled in the same manner as a single strand during manufacture of an implant.

This invention features an implant for medical use, including a structure having a body, the body constructed to include a plurality of single strands composed of at least a first material. The body further includes at least one multi-strand of radiopaque material incorporated among the single strands, the multi-strand having at least two side-by-side filaments of radiopaque material that lie substantially contiguous to each other over substantially the entire length of the multi-strand.

In some embodiments, each of the side-by-side filaments of the multi-strand is a monofilament of radiopaque material. Preferably, the diameter of each side-by-side filament is substantially the same as the diameter of the single strands.

This invention also features an implant having a body wall formed of a plurality of single strands of a first material establishing a first spacing pattern and a first wall thickness, such as an open braid or open weave pattern in a substantially tubular shape. The body wall further includes a plurality of multi-strands of radiopaque material interspersed with the single strands, each multi-strand having at least two side-by-side filaments of radiopaque material that lie substantially contiguous to each other, and each multi-strand joining in the first spacing pattern without substantial deviation from that pattern and without substantially altering the first wall thickness.

This invention further features a method for manufacturing an implant for medical use, including providing a plurality of carriers, each carrier having a single strand of a first material, and providing at least one carrier having a multi-strand of radiopaque material, the multi-strand having at least two side-by-side filaments of radiopaque material that lie substantially contiguous to each other over substantially the entire length of the multi-strand. The method further includes forming a body for the implant, preferably having a substantially constant wall thickness, utilizing both the single strands and the multi-strand.

In some embodiments, the carrier having the multi-strand is substantially the same as the carriers for the single strands. Each of the side-by-side filaments of the multi-strand is a monofilament of radiopaque material. Preferably, the diameter of each side-by-side filament is substantially the same as the diameter of the single strands. In a number of embodiments, forming the body includes establishing a first spacing pattern, and each multi-strand joins in the first spacing pattern without substantial deviation from that pattern. In certain embodiments, the first spacing pattern is one of an open braid pattern and an open weave pattern. In some embodiments, at least one multi-strand carrier is utilized for every dozen single-strand carriers, such as the machine having at least 42 carriers, and at least 6 of the carriers are loaded with the multi-strands of radiopaque material.

This invention also features a method of retro-fitting an implant forming machine having a plurality of carriers, each carrier designed to carry a single strand composed of at least one of a first material and a radiopaque material. The method includes selecting at least one of the plurality of carriers and loading the selected carrier with a multi-strand of radiopaque material. The multi-strand has at least two side-by-side filaments of radiopaque material that lie substantially contiguous to each other over substantially the entire length of the multi-strand. The method further includes forming a body for the implant utilizing both the single strands and the one or more multi-strands of radiopaque material.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by an implant for medical use, and method of making same, including a structure having a body constructed at least in part with a plurality of single strands composed of a first material. The body further includes at least one multi-strand of radiopaque material incorporated among the single strands, the multi-strand having at least two side-by-side filaments of radiopaque material that are in parallel with each other, that is, the filaments lie substantially contiguous to each other over substantially the entire length of the multi-strand. Suitable implants include flow diverters, stents, filters, surgical mesh, and other implants or portions thereof formed of strands of material and benefiting from enhanced radiopaque properties.

The term "strand" is intended in its broadest meaning to include a wire, a fiber, a filament, or other single elongated member. The term "radiopaque" is utilized for its normal meaning of being radiodense, that is, formed of one or more materials which inhibit the passage of electromagnetic radiation to increase visibility during imaging. Suitable radiopaque materials for use according to the present invention include platinum, chromium, cobalt, tantalum, tungsten, gold, silver, and alloys thereof.

Figure 1:
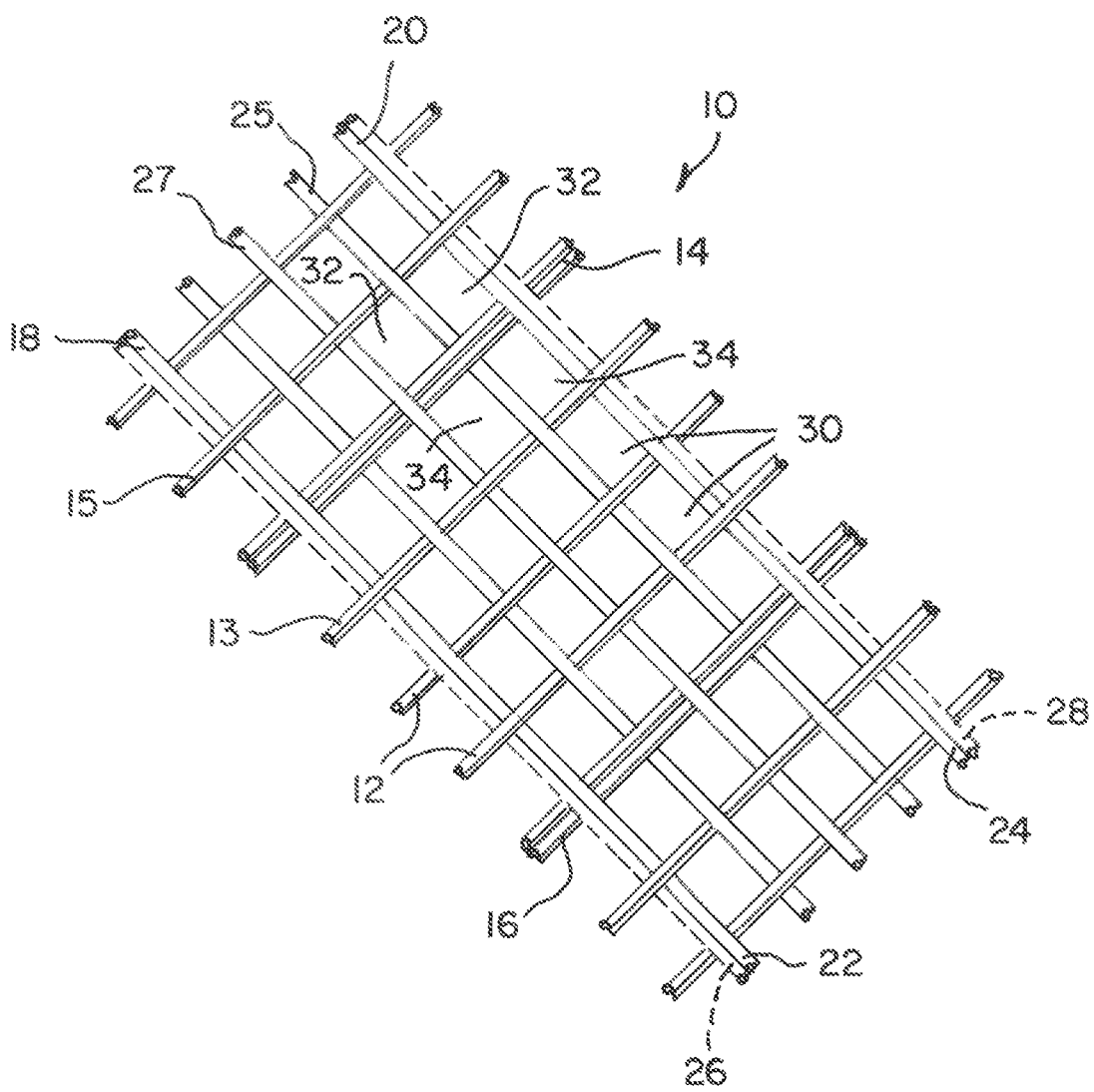
FIG. 1 is a schematic enlarged view of a portion of an implant body formed of single strands and one or more radiopaque multi-strands according to the present invention.

FIG. 1 is a schematic enlarged view of a portion of an implant body 10 according to the present invention formed of single strands 12 composed of at least a first material and one or more radiopaque multi-strands 14. In this construction, body 10 is woven to include at least a second multi-strand 16. In another construction, indicated by dashed lines, the body 10 further includes multi-strands 18 and 20 formed of monofilaments 22 and 24 each laid together with monofilaments 26 and 28, respectively.

The pattern of body 10, which is woven in some constructions and braided in other constructions, includes openings 30 defined by single strands 12 oriented in a first direction and by single strands 24 and 25 oriented in a second direction that is transverse to the first direction, for example. Body 10 further includes openings 32 and 34 defined on either side of multi-strand 14 by single strands 13 and 15 oriented in the same direction as multi-strand 14 and by single strands 24, 25 and 27 oriented in a transverse direction. In some constructions, openings 32 and 34 are slightly larger than openings 30 which are defined only by single strands; in other constructions, all openings 30, 32 and 34 are substantially the same. All of these constructions are considered to have substantially the same pattern as if body 10 were formed solely from single strands of material.

Since the multi-strands are braided, woven or otherwise laid in parallel to each other in the same manner as if single strands of radiopaque material were utilized, and especially when each filament of the multi-strand has the same diameter as the single strands, there is little or no mechanical impact to the performance of the implant, such as flexibility, ability to expand, and crimped profile.

Figure 2:
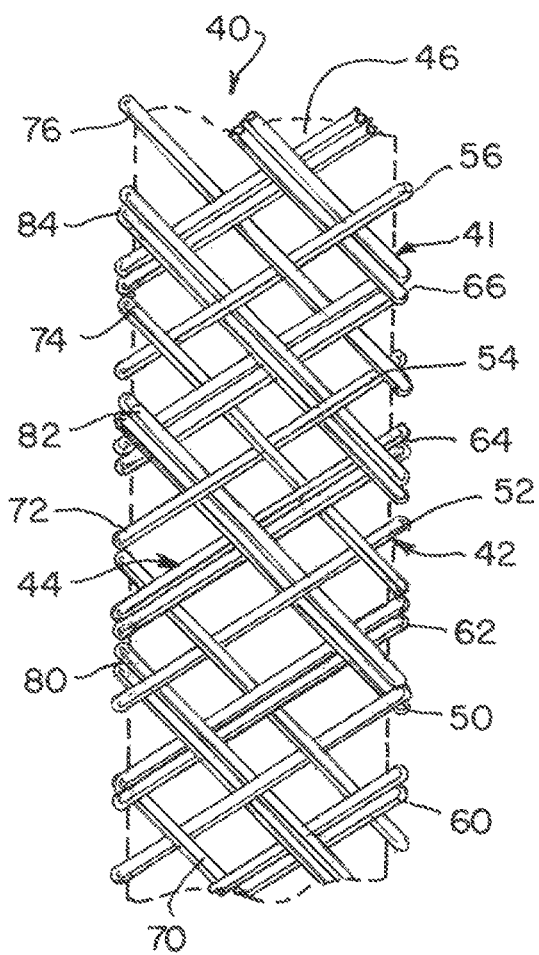
FIG. 2 is a schematic side view of a tubular braided implant having alternating single and multi-strands according to the present invention.

Tubular braided implant 40, FIG. 2, is a substantially cylindrical, hollow and porous structure such as a stent or a flow diverter having a body 41 formed of alternating single strands 42 and multi-strands 44 according to one construction of the present invention. Body 41 defines a central lumen 46. Single strands 50, 52, 54 and 56 are visible as oriented in a first direction and alternating with multi-strands 60, 62, 64, 66 and 68. Single strands 70, 72, 74 and 76 are visible as oriented in a second direction and alternating with multi-strands 80, 82 and 84. In some constructions, two or more of the separately numbered single strands are actually different portions of a single, continuous single strand as will be readily apparent to one of ordinary skill in the braiding and weaving art. Similarly, two or more of the separately numbered multi-strands are actually different portions of a single, continuous multi-strand.

Figure 3:
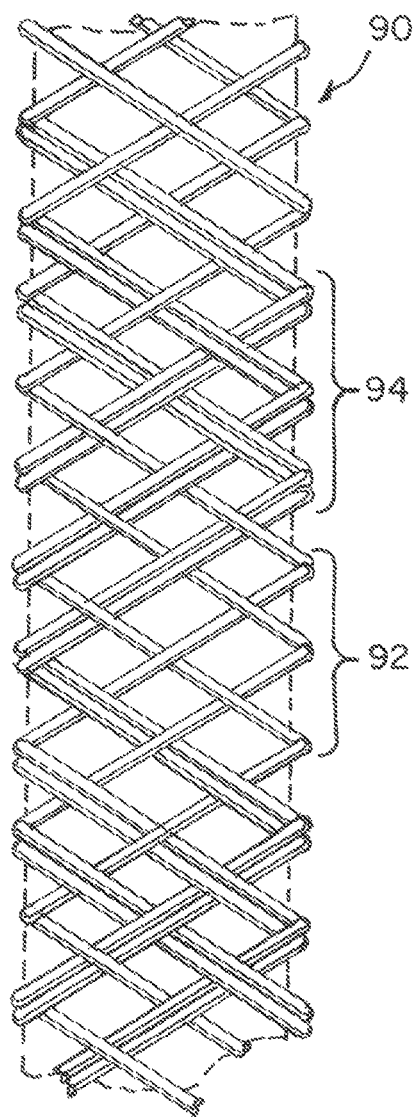
FIG. 3 is a schematic side view of a tubular braided implant having a more complex pattern of single and multi-strands according to the present invention.

FIG. 3 is a schematic side view of an alternative tubular braided implant 90 having a more complex pattern of three single strands 92 alternating with three multi-strands 94 according to another construction of the present invention. When viewed in a patient utilizing fluoroscopy or other imaging technique, implants 40 and 90 each will generate a different image, which aids a surgeon or other user to distinguish it from other implants and anatomical features. In some constructions, implants 40 and/or 90 define inner lumens ranging from 2.0 mm to approximately 5.0 mm in diameter.

This invention may also be accomplished by a method for manufacturing an implant for medical use, including providing a plurality of carriers, each carrier having a single strand of a first material, and providing at least one carrier having a multi-strand of radiopaque material, the multi-strand having at least two side-by-side filaments of radiopaque material that lie substantially contiguous to each other over substantially the entire length of the multi-strand. The method further includes forming a body for the implant, preferably having a substantially constant wall thickness, utilizing both the single strands and the multi-strand.

Figure 4:
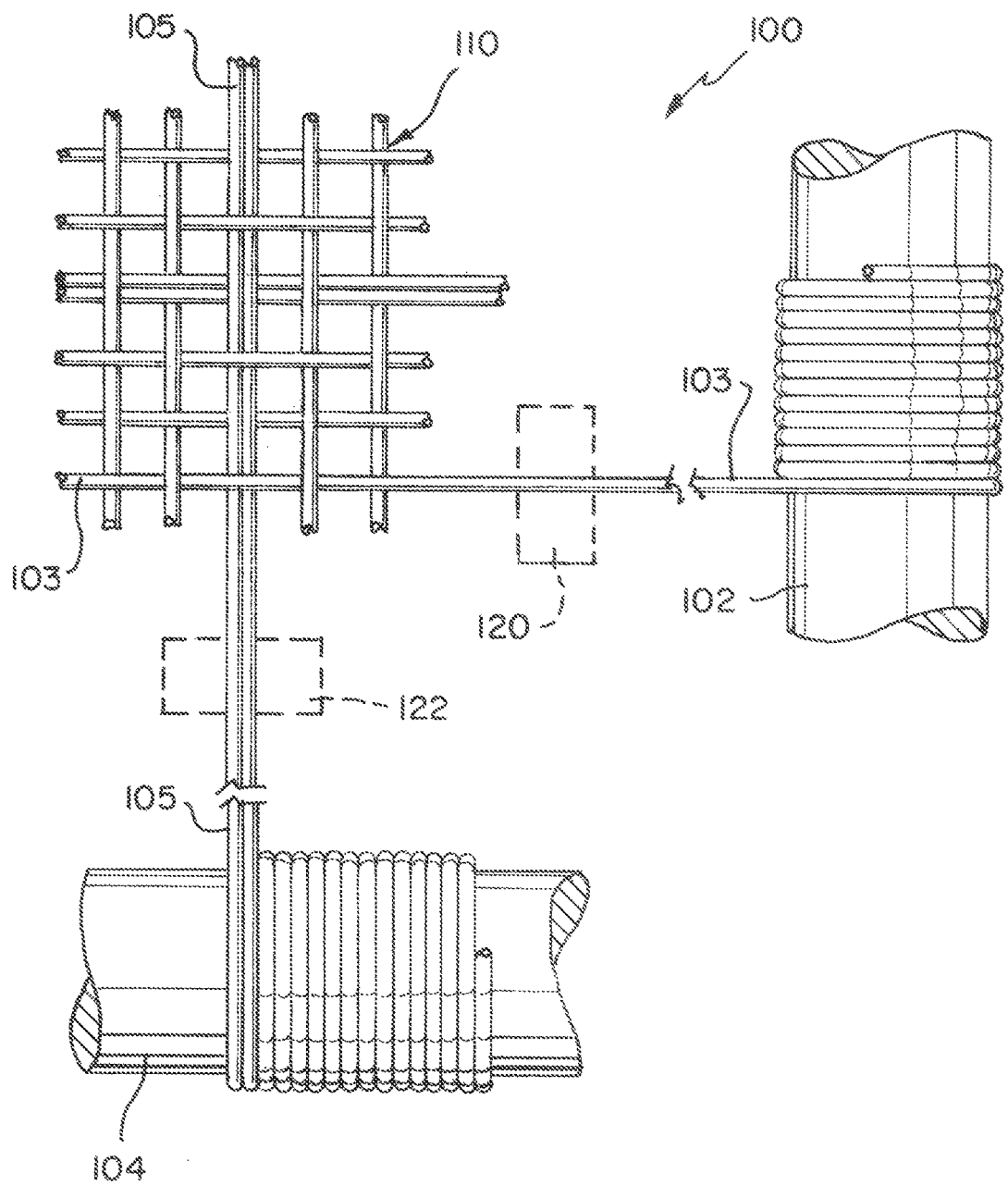
FIG. 4 is a schematic diagram a portion of an implant forming machine including a conventional carrier providing a radiopaque multi-strand during manufacture of an implant according to the present invention.

FIG. 4 is a schematic diagram, not to scale, of a portion of an implant forming machine 100 including conventional single-strand carriers 102 and 104 shown during manufacture of an implant 110 according to the present invention. Carrier 102 is loaded with single strand 103 while carrier 104 is loaded with a radiopaque multi-strand 105. Dashed components 120 and 122 represent conventional mechanisms for directing single strand 103 and multi-strand 105, respectively, to form implant 110 as will be understood by those of ordinary skill in the relevant field.

For ease of illustration, the pattern of strands shown in FIGS. 1-4 is a 1-over-1 braid-type pattern As will also be understood by those of ordinary skill after studying the present disclosure, other braid, knit, or weave patterns can be utilized according to the present invention, such as 1-over-2, 2-over-2, and other known patterns. Tension placed on each strand during implant formation is adjusted according to conventional techniques.

Another technique according to the present invention is to retro-fit an implant forming machine having a plurality of carriers such as carriers 102 and 104, each carrier designed to carry a single strand composed of at least one of a first material and a radiopaque material. The technique includes selecting at least one of the plurality of carriers, such as carrier 104, and loading the selected carrier with a multi-strand of radiopaque material. The multi-strand has at least two side-by-side filaments of radiopaque material that lie substantially contiguous to each other over substantially the entire length of the multi-strand. A body is formed for the implant utilizing both the single strands and the multi-strand.

In preferred techniques, each of the side-by-side filaments of the multi-strand is a monofilament of radiopaque material. In one construction, the carrier having the multi-strand is substantially the same as the carriers for the single strands. Each of the side-by-side filaments of the multi-strand is a monofilament of radiopaque material. Preferably, the diameter of each side-by-side filament is substantially the same as the diameter of the single strands. Forming the body includes establishing a first spacing pattern, such as an open braid pattern or an open weave pattern, and a first wall thickness, and each multi-strand joins in the first spacing pattern without substantial deviation from that pattern and without substantially altering the first wall thickness.

In certain techniques, at least one multi-strand carrier is utilized for every dozen single-strand carriers. Some machines have at least 42 carriers, such as 48 carriers, and at least 6 of the carriers, such as 8 carriers, are loaded with the multi-strands of radiopaque material. This still results in a 48-carrier braid but having double the number of radiopaque strands as when the 8 carriers are loaded with single strands of radiopaque material.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implant for medical use, comprising:
a structure having a body constructed to include;
a plurality of only single strands composed of at least a first non-radiopaque material and having at least one multi-strand of radiopaque material incorporated among the single strands, the multi-strand having at least two side-by-side filaments of radiopaque material that lie substantially contiguous to each other over substantially the entire length of the multi-strand, a diameter of each side-by-side filament is the same as a diameter of each of the single strands.

2. The implant of claim 1 wherein each of the side-by-side filaments of the multi-strand is a monofilament of radiopaque material.

3. An implant for medical use, comprising:
a structure having a body wall formed of a plurality of only single strands composed of at least a first non-radiopaque material, the single strands composed of at least a first non-radiopaque material establishing a first spacing pattern and a first wall thickness, the body wall including a plurality of multi-strands of radiopaque material interspersed with the single strands, each multi-strand having at least two side-by-side filaments of radiopaque material that lie substantially contiguous to each other, and each multi-strand joining in the first spacing pattern without substantial deviation from that pattern and without substantially altering the first wall thickness, a diameter of each side-by-side filament is the same as a diameter of each of the single strands.

4. The implant of claim 3 wherein each of the side-by-side filaments of the multi-strands is a monofilament of radiopaque material.

5. The implant of claim 3 wherein the first spacing pattern is one of an open braid pattern and an open weave pattern.

\* \* \* \* \*